United States Patent [19]

Bourrelly

[11] Patent Number: 5,615,439
[45] Date of Patent: Apr. 1, 1997

[54] DEVICE FOR CLEANING DUCTS IN MEDICAL INSTRUMENTS

[75] Inventor: Julien Bourrelly, Choisy Le Roi, France

[73] Assignee: La Technologie Avancee Medicale, Montreuil, France

[21] Appl. No.: 562,980

[22] Filed: Nov. 27, 1995

[30] Foreign Application Priority Data

Nov. 30, 1994 [FR] France .................................. 94 14363

[51] Int. Cl.$^6$ .................................. A46B 9/00; B08B 9/02
[52] U.S. Cl. .............................. 15/104.2; 15/160; 15/164; 15/168; 15/206
[58] Field of Search .................................. 15/104.2, 164, 15/168, 206, 160

[56] References Cited

U.S. PATENT DOCUMENTS

| | | | |
|---|---|---|---|
| 1,825,929 | 10/1931 | Voight . | |
| 2,421,647 | 6/1947 | Peterson | 15/168 |
| 2,824,322 | 2/1958 | Angelica | 15/164 |
| 3,613,664 | 10/1971 | Willson | 15/206 |
| 4,167,192 | 9/1979 | Arnold | 15/206 |
| 4,512,810 | 4/1985 | Gahlinger | 15/164 |
| 5,161,554 | 11/1992 | Fitjer . | |
| 5,168,593 | 12/1992 | Poji et al. . | |

FOREIGN PATENT DOCUMENTS

| | | | |
|---|---|---|---|
| 491788 | 4/1953 | Canada | 15/104.2 |
| 0467126 | 1/1992 | European Pat. Off. . | |

OTHER PUBLICATIONS

Preliminary Search Report issued in connection with French Application No. 94/00826.

Primary Examiner—David Scherbel
Assistant Examiner—Randall E. Chin
Attorney, Agent, or Firm—Wolf, Greenfield & Sacks, P.C.

[57] ABSTRACT

A device for cleaning the ducts of medical instruments for internal investigation or sample-taking, the device comprising an elongate cylindrical element and a brush provided at a first end of said element, the brush comprising substantially radial brushes mounted on a longitudinal spine. The device includes a brush support member constituted by a helically wound wire whose turns define a channel suitable for receiving the spine of the brush and having a portion of length substantially equal to the length of the brush along which the turns are spaced apart axially so as to allow the bristles of the brush to pass between them.

16 Claims, 2 Drawing Sheets

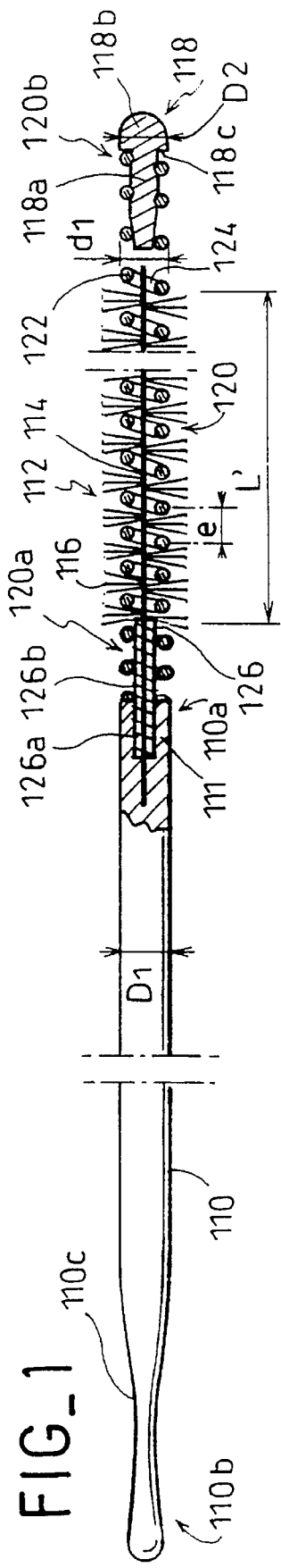
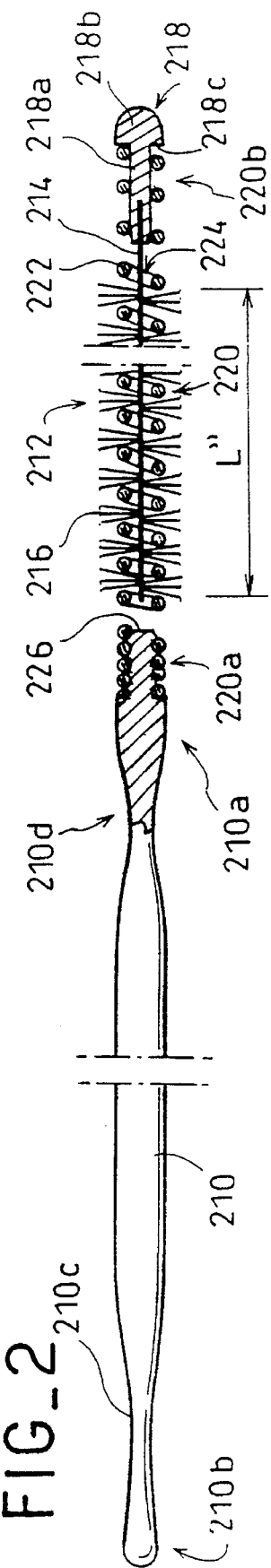
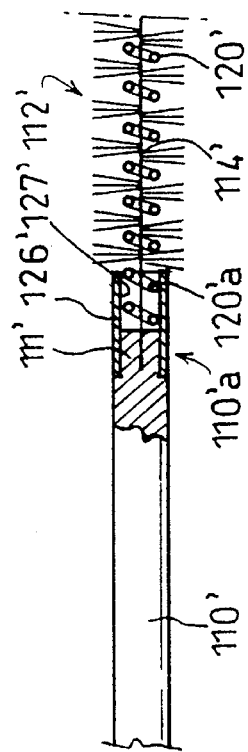

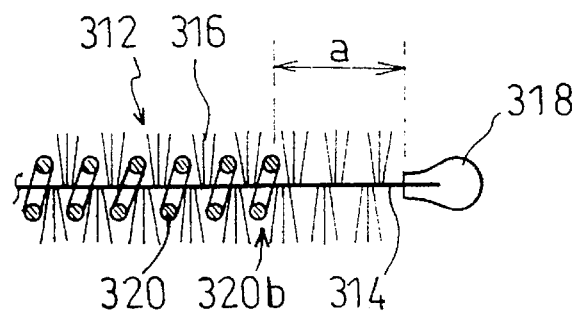
FIG_3
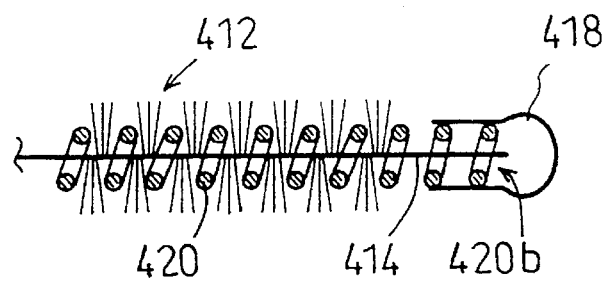
FIG_4
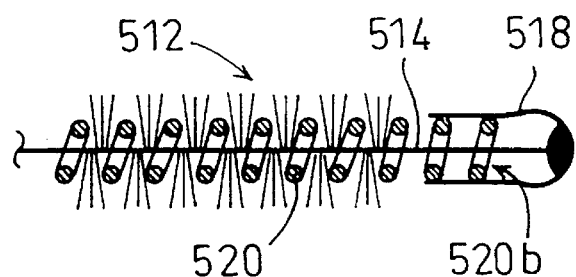
FIG_5
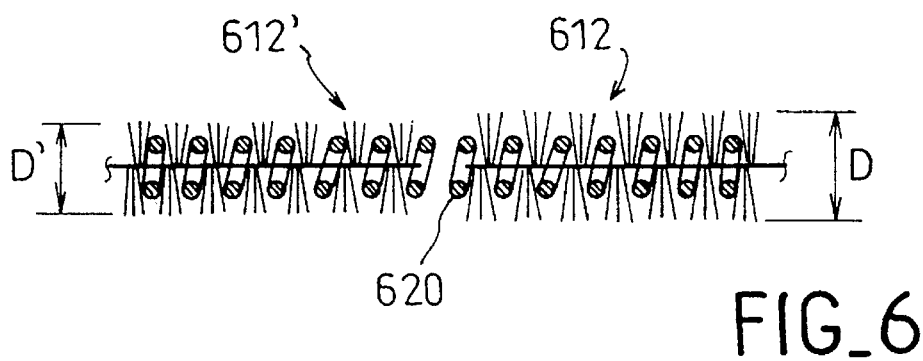
FIG_6
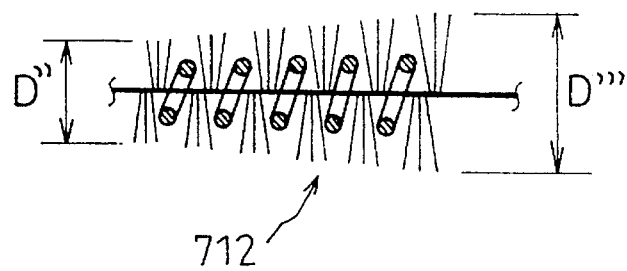
FIG_7

5,615,439

DEVICE FOR CLEANING DUCTS IN MEDICAL INSTRUMENTS

The present invention relates to a device for cleaning the ducts of medical instruments for internal investigation or sample-taking, the device comprising an elongate cylindrical element having a smooth outside surface and a brush provided at a first end of said element, the brush comprising substantially radial bristles mounted on a longitudinal spine.

The term "medical instruments for internal investigation or sample-taking" is used to designate instruments such as those conventionally used for endoscopic examinations, having a duct which is inserted into the body of the patient and into which medical tools are inserted such as optical appliances, sample-taking tools, or indeed surgical tools.

BACKGROUND OF THE INVENTION

Such instruments are relatively expensive and must therefore be capable of being used several times. Between two uses, they must be cleaned thoroughly and then decontaminated or sterilized. Cleaning the insides of the ducts turns out to be very difficult and requires a device of the above-specified type to be used like a bottle-brush or a ram-rod.

The radial size of the device must be small enough to enable it to be inserted in a duct whose diameter is generally small, e.g. of the order of 1 mm to 20 mm. In addition, the device must be sufficiently flexible to be capable of passing round any bends there may be in the duct, and in particular it must be capable of thoroughly cleaning any fork ones. In spite of its small radial size and its flexibility, the device must be relatively stiff axially, i.e. it must be strong enough to be pushed and pulled so as to be capable of being inserted along the entire length of the duct, which may as much as 1 or 2 meters, by being pushed in via one of the ends of the duct.

U.S. Pat. No. 5,168,593 shows a cleaning device in which the brush is connected to the cylindrical support element via a helical spring. More precisely, the spine of the brush is fixed to a first end of the spring, and the other end of the spring is fixed to the elongate cylindrical element.

That serves to make a flexible connection between the brush and the cylindrical element.

Unfortunately, those dispositions confer no flexibility to the brush itself.

It is not possible to impart radial flexibility only to the bristle-supporting spine of the brush without also making it axially flexible.

To enable the brush to pass through sharp bend zones of ducts, a first solution consists in providing it with a flexible spine. Unfortunately, axial flexibility impedes insertion of the brush into ducts and directly degrades its effectiveness. In any event, the mere fact of providing a long brush with a flexible spine is not satisfactory insofar as such a spine is not itself strong enough, so it breaks after being flexed repeatedly.

A second solution consists in making a brush that is very short (of length substantially equal to its diameter), and that is provided with a rigid spine, this relies on the fact that given the short length of the brush there is no need for its spine to bend significantly, even in zones of high curvature. Such a brush suffers from the drawback of being too short to clean certain particularly dirty ducts properly.

Thus, merely giving the device local flexibility in the connection zone between the brush and the supporting cylindrical element (itself sufficiently flexible radially and sufficiently stiff axially) does not suffice to ensure that the device is reliable.

OBJECT AND BRIEF SUMMARY OF THE INVENTION

An object of the invention is to remedy the drawbacks specified above.

To this end, the device further includes a brush support member mounted at the first end of the rod, the outside diameter of the support member being substantially equal to that of the rod, and the support member being suitable for supporting the brush substantially over the entire length thereof, said member being constituted by a helically wound wire whose turns define a channel suitable for receiving the spine of the brush, and having a length substantially equal to the length of the brush over which length the turns are spaced apart axially so as to allow the bristles of the brush to pass between them.

Because of these dispositions, the invention makes it possible to use a brush that is long and mounted on a flexible spine without its flexibility damaging cleaning effectiveness or brush insertion into the duct to be cleaned, the brush being supported axially by the support member without the axial support opposing the radial flexibility required for passing through zones of high curvature.

BRIEF DESCRIPTION OF THE DRAWINGS

The invention will be well understood and its advantages will appear more clearly on reading the following detailed description of embodiments shown as non-limiting examples.

The description refers to the accompanying drawings, in which:

FIG. 1 is a side elevation of a first embodiment of the device of the invention;

FIG. 1A shows a detail of a variant of the FIG. 1 embodiment;

FIG. 2 shows a second embodiment; and

FIGS. 3 to 7 are fragmentary views showing variant embodiments.

MORE DETAILED DESCRIPTION

The device of FIG. 1 comprises an elongate cylindrical element 110 and a brush 112 provided at a first end 110a of the element 110, the brush comprising substantially radial bristles 116 mounted on a longitudinal spine 114.

To avoid cluttering the drawing, the elongate cylindrical element has been truncated, and its length may lie in the range 1 meter to several meters, whereas its diameter generally lies in the range 1 mm to 20 mm. In the example shown, this elongate cylindrical element is constituted by a solid smooth rod of a plastics material (such as nylon, PVC or Teflon), e.g. made by extrusion. It may also be constituted by a reinforced plastics rod. In general, the outside surface of the element 110 is smooth. The element may therefore merely be coated in plastics material.

The end of the device situated adjacent to the brush 112 is provided with a protective endpiece 118, e.g. made of plastics material, having a rounded free end 118b of diameter D2 substantially equal to the running diameter D1 of the rod 110.

The term "running" diameter is used to designate the diameter it has over most of its length, excepting possible narrowed portions. Its running diameter is also its maximum diameter.

The device includes a brush support member. To increase effectiveness, it is advantageous for the brush to be relatively long.

As mentioned above, when the brush is long, it is essential for it to be flexible so as to be capable of negotiating the bends in the ducts of the instruments it cleans. The same requirements concerning radial flexibility and relative axial stiffness apply to the brush as to the remainder of the device. A mere long flexible spine does not satisfy these requirements and runs the risk of breaking.

The support member makes it possible to fit the device with long brushes, of length much greater than their diameter, e.g. lying in the range five times to fourteen times the diameter, or even more.

The support member 120 of FIG. 1 is mounted on the first end 110a of the rod 110 and has an outside diameter d1 substantially equal to the running diameter D1 of the rod. It supports the brush 112 along the entire length L' thereof. The member 120 extends beyond the end 110a of the rod through a distance that is greater than the length of the brush. Likewise, the support member 220 of FIG. 2 supports the brush 212 over its entire length L".

The support member 120 or 220 is constituted by a helically wound wire, whose turns 122 or 222 define a channel 124 or 224 suitable for receiving the spine of the brush. At least over a length of the support member that is at least as long as the brush, the turns are axially spaced apart from one another so as to allow the bristles of the brush to pass between them.

The bristles of the brush are preferably helically disposed, and on each turn of the brush helix they are preferably grouped together in tufts of three or four or more bristles. The spacing "e" between the turns of the support member allows an entire turn of brush bristles to pass through, and is therefore of the order of three times to twenty times the thickness of a bristle.

As can be seen in FIGS. 1 and 2, the helical pitch of the support member in that portion thereof where the turns are spaced apart is substantially equal to the helical pitch formed by the bristles of the brush. It will therefore be understood, as explained below, that the brush and the support member can be put into place relative to each other by screwing motion.

In FIG. 1, the end 110a of the rod 110 is provided with a coupling Sleeve 126 suitable for co-operating with the first end 120a of the support member 120 to couple it to the rod 110. The sleeve is substantially cylindrical and its running radius is less than the running radius of the rod. The difference between these radii is substantially equal to the thickness of the wire which constitutes the support member. Thus, even in the region of the coupling between the rod and the support member, the outside diameter of the member is kept less than or substantially equal to the running diameter of the rod. The wire constituting the support member may be a metal wire and it is preferable to ensure that it does not project beyond the diametral size of the rod in order to avoid scratching the duct being cleaned. In contrast, and insofar as the rod is smooth, there is no harm in the outside diameter of the support member being slightly smaller than the diameter of the rod.

In this respect, it should be observed that the bristles of the brush prevent any direct contact between the support member and the duct to be cleaned along the brush-supporting length of the support member.

In FIG. 1, the spine 114 of the brush is fixed to the first end 110a of the rod. The end of this spine may be engaged in a short axial bore in the rod and it may be held therein by adhesive. Under such circumstances, it naturally passes through an axial bore in the sleeve 126. The brush is thus permanently secured to the rod 110.

Between two cleaning operations, it is important to clean and decontaminate the device. Naturally, it is then preferable to be able to have total access to the bristles of the brush. For that purpose, the support member 120 of FIG. 1 is dismountable and it may be mounted or dismounted on the first end of the rod 110 by screwing movement relative to the brush. In the mounting direction, the screwing motion continues until the end 120a of the support member co-operates with the sleeve 126.

The support member 120 is held axially by being screwed onto the brush 112.

In FIG. 1, it can be seen that the sleeve is constituted by a separate element fixed to the end 110a of the rod. The sleeve may be constituted by a rigid part, e.g. made of metal, which, by rigidly supporting the end turns of the support member, serves to initiate curving thereof when the device is inserted into bends of ducts to be cleaned. It is important to prevent the support member from becoming slightly offset radially relative to the rod in order to ensure that it does not come into contact with the inside walls of the duct to be cleaned.

The first end 110a of the rod 110 has a cylindrical cavity 111. The sleeve 126 has a first portion 126a received in the cavity 111 and fixed to its walls. The sleeve has a second portion 126b which projects beyond the first end 110a of the rod. It is this second portion which co-operates with the end 120a of the support member. The outside diameter of the second portion 126b is less than or equal to the inside diameter of the support member 120. This second portion serves to guide the support member while it is being screwed, and above all, when said member is in place, it serves to prevent it moving transversely relative to the axis of the spine 114. As mentioned above, the sleeve has an axial bore matching the size of the spine of the brush.

The endpiece 118 has a first portion 118a of diameter that matches that of the channel defined by the turns of the support member 120, and a second portion 118b having a rounded end. These two portions are united via a shoulder 118c suitable for co-operating with the free end 120b of the support member. In the embodiment of FIG. 1, the endpiece may be fixed permanently to the support member 120, e.g. by adhesive, or it may be screwed into it, in which case it should have an appropriate thread.

The second portion 118b of the endpiece of diameter greater than the outside diameter of the support member 120 serves to ensure that the support member does not come into contact with the duct to be cleaned.

FIG. 1A shows a variant method of assembly making use of a hollow cylindrical sleeve 126'. In this variant, the end 110'a of the rod 110' has a shoulder and an end portion of smaller diameter 111'. The sleeve 126' is fitted onto said end portion 111' and is fixed thereto. Its outside diameter is no greater than the outside diameter of the rod 110'.

In this position, the cylindrical cavity 127' formed between the end of the rod and the free end of the sleeve 126' serves as a housing for the first end 120'a of the support member 120'. This shape ensures that the first end 120'a cannot move relative to the axis of the spine 114' of the brush 112' on which the support member is screwed.

In the embodiment of FIG. 2, where elements common to FIG. 1 are given the same references, plus 100, the first end 220a of the support member is fixed to the sleeve 226. The brush 212 is then suitable for being installed in said support member by screwing motion and of being removed therefrom by unscrewing. It is held axially in the support member because its bristles pass between the turns thereof. Like the sleeve 126, the sleeve 226 is substantially cylindrical and has a running radius that is less than the running radius of the rod 210, with the difference between the radii being substantially equal to the thickness of the wire from which the support member is made.

In the example shown, the sleeve 226 is merely constituted by a smaller diameter end portion of the end 210a of the rod. Clearly, it will be possible to use a sleeve similar to the sleeve 126 described above and in the same manner. Nevertheless, there is no need for it to have an axial bore insofar as the spine of the brush is not engaged therein.

The end 220a of the support member is fixed to the sleeve 226 by any appropriate means, such as adhesive or forced screwing. If screwing is used, the sleeve 226 may have a thread.

The protective endpiece 218 has a first portion 218a suitable for fixing to the spine 214 of the brush, and of a diameter that matches the diameter of the channel defined by the turns of the support member, which first portion is united to a rounded end 218b by a shoulder 218c suitable for co-operating with the free end of the support member. The brush 212 is thus properly put into place when the shoulder 218c comes into abutment against the first turn at the free end 220b of the support member.

FIGS. 3 to 5 show variants in which the endpieces can be made of metal. To avoid overloading the FIGS., only the end regions of the brushes are shown. The support members and the brushes are analogous in structure to those described above.

In FIG. 3, the endpiece 318 is directly fixed to the free end of the spine 314 of the brush 312, by any appropriate means such as crimping, adhesive, or screwing. The brush therefore projects a small distance "a" beyond the free end 320b of the support member 320. Nevertheless, it should be observed that this free end is not aggressive since it is embedded in the bristles 316 of the brush. Furthermore, the distance "a" is small enough for lack of any support at the end of the brush to have no ill effect on its effectiveness nor on the strength of the spine. The diameter of the endpiece 318 may be smaller than that of the support member.

In FIG. 4, the endpiece 418 is fitted onto the free end 420b of the support member 420 and it may be swaged onto it so as to be fixed permanently thereto. The spine 414 of the brush advantageously extends into the inside of the endpiece.

In FIG. 5, the endpiece 518 is likewise fitted on the free end 520b of the support member 520. However, this endpiece is fixed directly to the end of the spine 514 of the brush 512 by adhesive, welding, or any other analogous means. The assembly constituted by the brush 512, and the endpiece 518 can thus be removably mounted relative to the support member 520.

The endpieces 318, 418, and 518 are rounded to avoid damaging the ducts cleaned by means of the device.

FIG. 6 shows two brushes 612 and 612' disposed in succession in the support member 620. These two brushes can thus be located one after the other at the first end of the rod. They are of different diameters D and D'. They may be separate as shown in the FIG., or they may be united on a common spine.

It has been observed that duct cleaning is more effective when the diameter of the bristles of the brush used is very slightly greater than the inside diameter of the duct. It happens that the diameter of ducts in medical instruments for internal investigation or sample-taking varies depending on the type of examination or operation that is performed with such instruments, and also with the morphology and with the age of the patient. When fitted with a plurality of brushes of different diameters, the device thus serves to clean different instruments all with the same effectiveness. Depending on the diameter of the duct being cleaned, one of the brushes will contribute most to cleaning, while the bristles on the other brush(es) are either bent back or else do not come into contact with the duct to be cleaned.

FIG. 7 shows a brush 712 whose diameter varies along its length, increasing from a small diameter D" to a larger diameter D'". This increase may be progressive as shown in the figure, in which case the brush is frustoconical. It may also be gradual or in steps so the brush may have cylindrical portions and frustoconical portions. Such a shape ensures that there is always at least one region of the brush having bristles of the right diameter for very effective cleaning of the duct.

The brush 712 may be provided on its own or in association with one or more other brushes, like the cylindrical brushes 612 and 612'.

In the vicinity of its second end 110b, the rod 110 of FIG. 1 has a portion of reduced section 110c of flexibility that is greater than that of its running portion. This section preferably tapers progressively, thereby enabling the flexibility of the rod to vary progressively. The same applies to the rod 210. In some cases, e.g. when cleaning ducts that have very sharp bends locally, it is preferable to insert the device via the second end 110b or 210b of the rod. The highly flexible section of smaller diameter can pass round bends without difficulty, thereby enabling the device to be inserted in full.

In FIG. 2, it can be seen that the rod 210 has another portion of smaller diameter 210d situated in the vicinity of the first end 210a. This portion 210d gives a high degree of flexibility locally just before the brush 212.

The device may be fitted with a second brush situated at the second end of the rod. The second brush may be fitted with a support member analogous to that fitted to the first brush and is advantageously shorter and wider than the first brush. Under such circumstances, it is the second brush which is inserted first into the duct to be cleaned.

I claim:

1. A device for cleaning the ducts of medical instruments for internal investigation or sample-taking, the device comprising an elongate cylindrical rod having a smooth outside surface and a brush provided at a first end of said rod, the brush comprising substantially radial bristles mounted directly on a longitudinal spine, wherein the device further includes a brush support member mounted at the first end of the rod, the outside diameter of the support member being substantially equal to that of the rod, and the support member being suitable for supporting the brush substantially over the entire length thereof, said member being constituted by a helically wound wire whose turns define a channel wherein the spine extends substantially straight and longitudinally through the channel, the member having a length substantially equal to the length of the brush over which length the turns are spaced apart axially so as to allow the radial bristles of the brush to pass between them.

2. A device according to claim 1, wherein the first end of the rod is provided with a coupling sleeve suitable for co-operating with a first end of the support member for coupling it to the rod, said sleeve being substantially cylindrical and having a running radius that is smaller than the running radius of the rod, the difference between said radii being substantially equal to the thickness of the wire constituting the support member.

3. A device according to claim 1, wherein the first end of the rod has a portion of smaller diameter and is provided with a hollow cylindrical sleeve fitted on said portion, and the cylindrical cavity between the first end of the rod and the free end of the sleeve serves as a housing for the support member.

4. A device according to claim 2, wherein the first end of the rod has a cylindrical cavity, and the coupling sleeve has a first portion housed in said cavity and fixed to the walls thereof, a second portion projecting beyond the first end of the rod and suitable for cooperating with the support member, and an axial bore of dimensions adapted to receive the spine of the brush.

5. A device according to claim 1, wherein the spine of the brush is fixed to the first end of the rod, and the support member is suitable for being mounted at the first end of the rod by screwing motion relative to the brush.

6. A device according to claim 2, wherein the support member is fixed to the sleeve, and the brush is suitable for being installed in said support member by screwing motion.

7. A device according to claim 1, wherein the length of the brush is greater than three times the diameter of said brush.

8. A device according to claim 1, wherein the diameter of the brush varies along its length.

9. A device according to claim 1, including at least two brushes disposed one after the other at the first end of the rod, and having different diameters.

10. A device according to claim 1, wherein the rod has in the vicinity of at least one of its ends is a progressively reduced section of greater flexibility than the other portions of said rod.

11. A device according to claim 1 further including an endpiece mounted on the end of the brush support member opposite the first end of the rod.

12. A device according to claim 11, wherein the endpiece is fixed to the support member.

13. A device according to claim 11, wherein the endpiece has a first portion of a diameter that matches that of the channel defined by the turns of the support member and a second portion in the form of a rounded end united with said first portion by a shoulder suitable for cooperating with the support member.

14. A device according to claim 12, wherein the endpiece is fixed to the spine of the brush.

15. A device according to claim 12, wherein the endpiece is fitted over the support member.

16. A device according to claim 1, including at least two brushes disposed one after the other at the first end of the rod.

* * * * *